United States Patent
Schaft

(10) Patent No.: US 7,349,081 B2
(45) Date of Patent: Mar. 25, 2008

(54) METHOD AND DEVICE FOR CHECKING THE INTEGRITY OF A GLASS PROTECTING TUBE FOR THE SPIRAL-WOUND FILAMENT OF AN INFRARED RADIATOR HEAT SOURCE

(76) Inventor: Volker Schaft, Barkenkoppel 38, 22391 Hamburg (DE)

( * ) Notice: Subject to any disclaimer, the term of this patent is extended or adjusted under 35 U.S.C. 154(b) by 103 days.

(21) Appl. No.: 11/428,651

(22) Filed: Jul. 5, 2006

(65) Prior Publication Data
US 2006/0274307 A1 Dec. 7, 2006

(30) Foreign Application Priority Data
Jan. 7, 2004 (EP) .................................. 04000117

(51) Int. Cl.
*G01N 21/00* (2006.01)
(52) U.S. Cl. .................. 356/239.1; 356/239.2
(58) Field of Classification Search ...................... None
See application file for complete search history.

(56) References Cited
U.S. PATENT DOCUMENTS 3,533,704 A   10/1970   Krenmayr
3,777,171 A   12/1973   Hollenbeck
4,483,615 A * 11/1984   Bieringer et al. ........ 356/239.1
4,492,477 A *  1/1985   Leser ........................ 356/430
6,822,735 B2* 11/2004   Kim et al. ............... 356/239.1

FOREIGN PATENT DOCUMENTS
EP    1 553 403    7/2005

* cited by examiner

*Primary Examiner*—Michael P. Stafira
(74) *Attorney, Agent, or Firm*—Kelly Lowry & Kelley LLP

(57) ABSTRACT

In order to be able to check reliably glass protecting tubes for spiral-wound filaments of an infrared radiator heat source with respect to damages due to breaking, a device and method are provided for checking the integrity of a glass protecting tube, in particular made of quartz glass, is proposed with the invention for the spiral-wound filament of an infrared radiator heat source, whereby an analysis light beam is introduced into and passed through the material of the quartz protecting tube and whereby the analysis light beam coming out of the quartz protecting tube is detected and its intensity and/or wave length and/or phase is analyzed and whereby it is ascertained by means of the analysis if the quartz protecting tube is damaged or intact.

14 Claims, 3 Drawing Sheets

METHOD AND DEVICE FOR CHECKING THE INTEGRITY OF A GLASS PROTECTING TUBE FOR THE SPIRAL-WOUND FILAMENT OF AN INFRARED RADIATOR HEAT SOURCE

BACKGROUND OF THE INVENTION

In technical heating methods, medium wave infrared radiation is often used in the most various fields in order to feed process heat. This being medium wave sources of radiation such as spiral-wound filaments which are enclosed by a clear glass protecting tube translucent for infrared radiation or several such tubes often serve as heat sources. These tubes are open on the front side since it is not necessary to protect the spiral-wound filaments from the ambient air—they can be operated in air in the medium wave infrared range without oxidation and remain stable for several years. The glass protecting tube is rather primarily used for the electrical protection.

Since the ambient air is substantially without influence on the spiral-wound filament, a break of the glass protecting tube does not result, differently from for example a break of the glass bulb of a traditional filament bulb, compulsorily to a change of the electrical behaviour of the infrared radiator heat source. Thus the risk does exist that such a break remains unnoticed.

Apart from the fact that with a broken glass protecting tube the electric insulation is not given any longer, it is necessary when using these infrared radiator heat sources in sensitive processes to avoid a soiling of the material to be radiated with broken glass pieces or to stop immediately the process in case of a glass break so that all the parts which can come into contact with glass broken pieces can be eliminated and so that a soiling of further process material does not take place.

In U.S. Pat. No. 3,533,704 a method and a device are disclosed for which glass objects, for example glass tubes, and are tested with respect to breaks by means of light in a kind of quality control after the manufacturing. To this purpose light is introduced frontally into the glass object and the light coming out of the glass is checked with a detector. Intensity fluctuations indicate a break.

In U.S. Pat. No. 3,777,171 a similar method and a comparable device are indicated which serve for the detection of occlusions or non-homogeneities in glass objects, for example in glass tubes.

The methods and device mentioned in the two mentioned printed documents serve for the quality control and are not provided for the use for the control of a glass protecting tube during the operation of an infrared radiator heat source or another insitu control.

Before this background the aim of the invention is to create a method and a device with which the integrity of a glass protecting tube can be reliably checked for a spiral-wound filament of an infrared radiator heat source during operation and a break thereof can be surely ascertained.

SUMMARY OF THE INVENTION

For achieving this aim, the invention proposes a method according to claim 1 and a device according to claim 8.

Advantageous embodiments of the method are indicated in the claims 2 to 7, improvements of the device in the claims 9 to 14.

The invention is based on the idea that a break determines a change of the optical properties of the glass protecting tube. Due to broken glass edges in the material the light conductibility of the material changes (there are partial or even total reflections on such broken glass edges) and interference phenomena can take place which can cause a change of the phase of the light or of the intensity. Until now one can ascertain changes of the optical properties of glass, in particular of quartz glass already before a visible break takes place when the material already encountered crystalline changes.

This fact is used in that analytical light is coupled into the material of the glass protecting tube and is guided through the material. At the end of the material, the analytical light is detected and analyzed for example with respect to intensity, phase or wavelength. In case of an intact glass protecting tube, a calibration then takes place, i. e. the analysis values are determined for an intact glass protecting tube and are treated as standard values for an intact glass protecting tube. If there then results during the operation of the infrared radiator heat source variations of these analysis values in a predetermined extent situated outside a tolerance limit, a break of glass can be deduced.

This being, it is provided to guide the analysis light from a frontal side of the glass protecting tube in its longitudinal direction to the opposite front side. In this manner, the integrity of a comparably big section of the glass protecting tube can be checked or controlled with a single passage of light.

Since glass protecting tubes behave in intact condition substantially as an optical guide and have practically no radiation loss, it is possible to deviate the beam either by means of means for deflection such as for example reflectors, bent light guiding fibers or the like and to let pass through the same glass protecting tube at another place again in the opposite direction or to let pass through several glass protecting tubes equally optically connected in series the one after the other before a detection and analysis take place. To this purpose the device according to the invention has apart from a light source means for introducing the analysis light beam into the material of the glass protecting tube, a detector as well as means for analyzing the analysis light beam, means for deflecting the analysis light beam from a front side of the glass protection tube to the opposite new entry offset in location into the same front side of the glass protecting tube or for introducing the analysis light beam into a front side of a further glass protecting tube parallel to is longitudinal direction and the detector is placed on the front side of a glass protecting tube from which the analysis light beam comes out last.

As analysis light beam a laser light beam is preferred since laser light on the one hand can be produced with a good reproducibility so that a calibration, once carried out, can be held and since a laser light beam is very good directed, it hardly produces scattered light. The latter implies that the beam can simply be completely loaded into the material and that with an intact glass protecting tube there does not come any light away from the light path provided and thus does not impair the analysis result.

In order to compensate variations in the light source and not to have to fall back to a calibration which has once been carried out, a reference light beam can be split off from the analysis light beam which detects and analyzes without going through the glass protection tube and which is compared with the analysis light beam coming out of the glass protecting tube. In case of variations defined and fixed beforehand, a break of the glass protecting tube can then be displayed. The distribution of the light beam can take place for example by means of a semi permeable mirror as beam splitter.

The method or the device according to the invention can, if a break is ascertained, for example trigger an alarm and automatically stop the production process.

The invention will be explained in detail with reference to the embodiments represented in the attached figures. Further advantages and characteristics of the invention can be recognized from this description.

DETAILED DESCRIPTION OF THE PREFERRED EMBODIMENT

Figure 1:
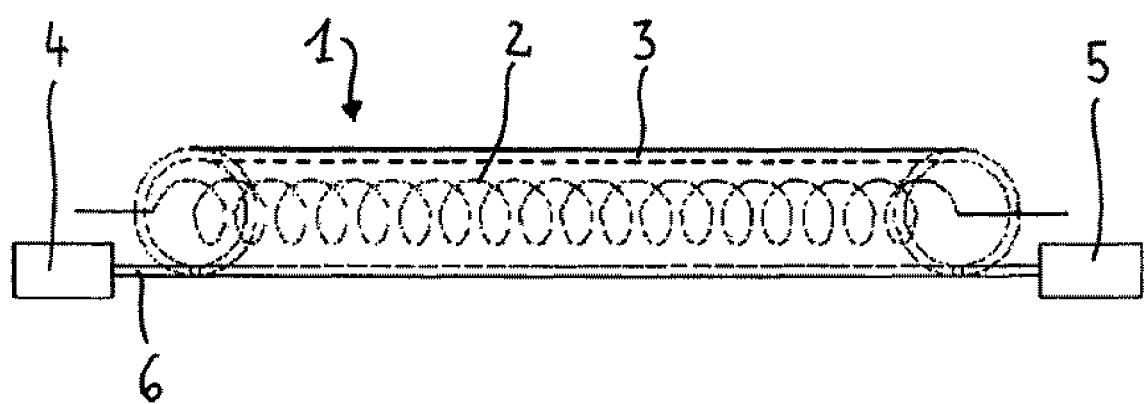
FIG. 1 shows a first embodiment of a device according to the invention for checking the integrity of a glass protecting tube.

In FIG. 1 an infrared radiator heat source 1 which has a device according to the invention is shown schematically. The infrared radiator heat source 1 is formed in this example by a spiral-wound filament 2 and a cylindrical glass protecting tube 3 of quartz glass which surrounds this filament which is open on both front sides.

A light source 4, for example a laser which produces an analysis light beam 5, is provided to check the integrity of the glass protecting tube 3. This beam is coupled into the material of the glass protecting tube 3 for example by means of focussing optics or of a light guide on a front side of the glass protecting tube 3.

On the opposite front side, the analysis light beam 6 comes out of the glass protecting tube 3 and falls into the detector which is placed there. The analysis light guide is analyzed there and if a difference is ascertained with respect to the calibration which has been carried out, a break of the glass protecting tube 3 is ascertained. A corresponding signal can then be emitted.

Figure 2:
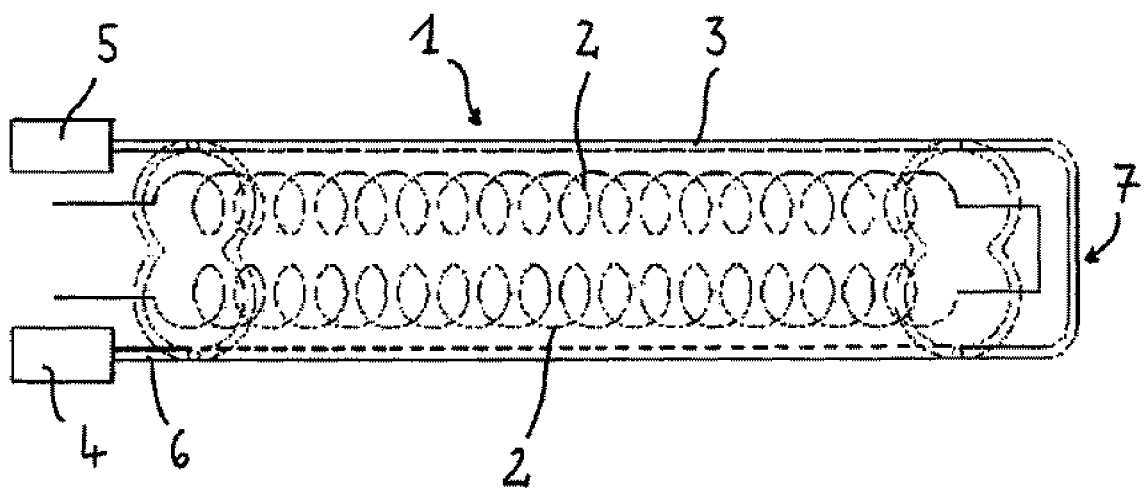
FIG. 2 shows a second embodiment of a device according to the invention for checking the integrity of a glass protecting tube.

A similar embodiment is shown in FIG. 2. In the infrared radiator heat source 1 which is represented there two spiral-wound filaments 2 are placed parallel in a glass protecting tube 3 in which two parallel lodging spaces are configured. In this example, the light source 4 and the detector 3 are placed on a front side of the glass protecting tube 3. The analysis light beam 6 is introduced on the front side into the material of the glass protecting tube 3, comes out again on the opposite front side and is deflected in the area 7 with appropriate means (mirror, light guiding fiber, prisms or the like) so that it comes at another sport and in opposite direction again into the material of the glass protecting tube 3 and passes again through this tube. In this manner the integrity of the glass protecting tube 3 is checked along two paths and thus still more precisely. Moreover the light source 4 and the detector 5 can be placed on one side of the glass tube 3 which can save space and which can be advantageous with respect to the supply with operating voltage as well as signal lines.

Figure 3:
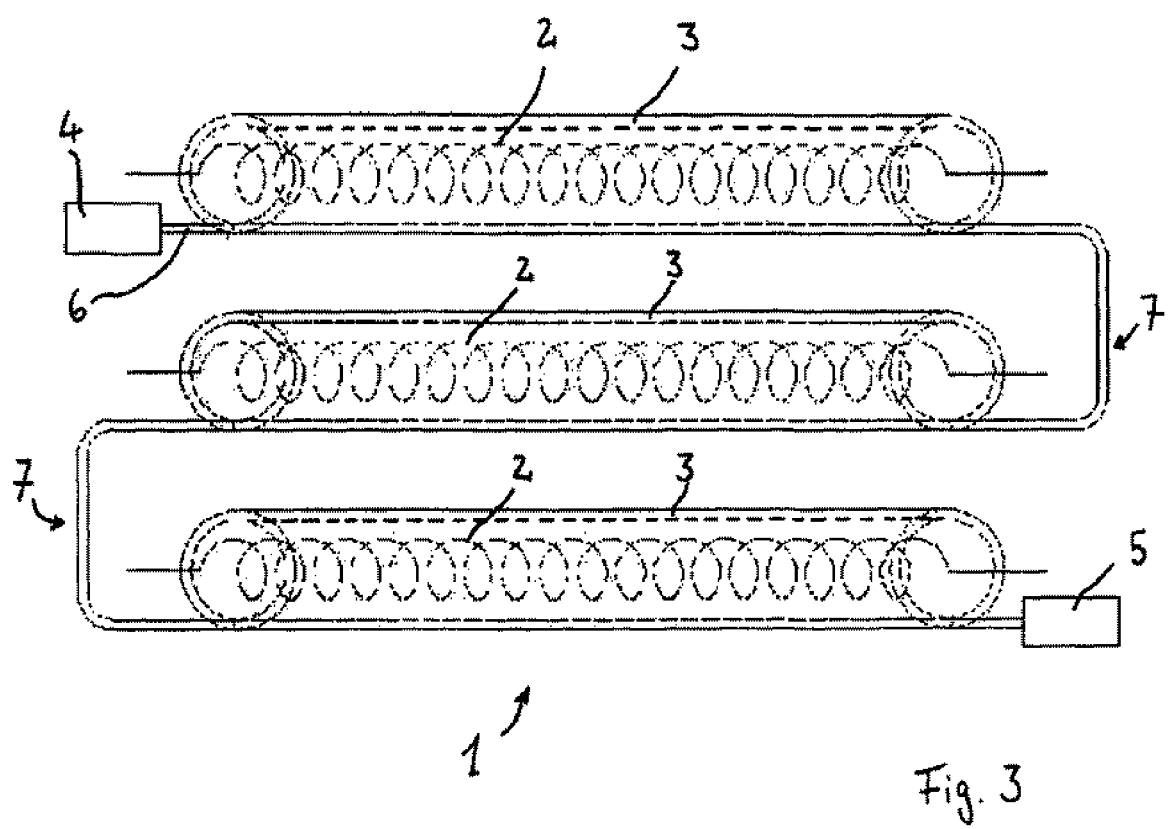
FIG. 3 shows an embodiment of a device according to the invention for checking the integrity of several glass protecting tubes.

The infrared radiator heat source shown in FIG. 3 contains three parallel arranged spiral-wound filaments 2 surrounded respectively by an appropriate glass protecting tube 3. Here the analysis light 6 produced by the light source 4 is passed through the three glass protecting tubes 3 in the longitudinal direction thereof before it comes at the end of the third glass protecting tube 3 onto the detector 5. The analysis light 6 is respectively deflected in the areas 7 as explained above to FIG. 2.

This alternative embodiment allows the simultaneous checking of several glass protecting tubes 3 due to their optical series connection. The number of the glass tubes 3 connected in series is not limited to three but is principally any. A limit is set only by the absorption in the glass since this may not be too high for a reliable analysis.

What is claimed is:

1. A method for checking the integrity of a glass protecting tube, in particular of quartz glass, for the spiral-wound filament of an infrared radiator heat source, whereby an analysis light beam is introduced into and passed through the material of the quartz protecting tube and whereby the analysis light beam coming out of the quartz protecting tube is detected and its intensity and/or wave length and/or phase is analyzed and whereby it is ascertained by means of the analysis if the quartz protecting tube is damaged or intact, characterized in that the analysis beam is introduced on the front side into the material of the glass protecting tube and is passed through it in longitudinal direction.

2. A method according to claim 1, characterized in that the analysis light beam is introduced on a first front side of the quartz protecting tube into the material of the quartz protecting tube, is deflected or reflected on an opposite second front side of the quartz protecting tube to a further passage through the quartz protecting tube at another location and in opposite direction and is then detected and analyzed on the front side of the quartz protecting tube on which it has first been introduced into the material.

3. A method according to claim 1, characterized in that the analysis light beam is guided through several quartz protecting tubes the one after the other respectively in longitudinal direction and is detected and analyzed only after having passed through the last quartz protecting tube.

4. A method according to claim 3, characterized in that the analysis light beam is divided before the first introduction into a front side of a quartz protecting tube and thus a reference light beam is split off and that the reference light beam is detected and analyzed without passing through the quartz protecting tubes for comparison together with the analysis light beam coming out of the quartz protecting tube.

5. A method according to claim 1, characterized in that laser light is used as analysis light.

6. A method according to claim 1, characterized in that the analysis light beam is guided through several quartz protecting tubes the one after the other respectively in longitudinal direction and is detected and analyzed only after having passed through the last quartz protecting tube.

7. A method according to claim 6, characterized in that the analysis light beam is divided before the first introduction into a front side of a quartz protecting tube and thus a reference light beam is split off and that the reference light beam is detected and analyzed without passing through the quartz protecting tubes for comparison together with the analysis light beam coming out of the quartz protecting tube, and characterized in that laser light is used as analysis light.

8. A device for checking the integrity of a glass protecting tube (3), in particular of quartz glass, for the spiral-wound filament (2) of an infrared radiator heat source (1) with:
a light source (4) for producing an analysis light beam (6);
means for introducing the analysis light beam (6) into the material of the glass protecting tube (3);

a detector (5) for detecting the analysis light beam (6) coming out of the glass protecting tube (3); and means for analyzing the intensity and/or wave length and/or phase analysis light beam (6);

characterized in that the means for introducing the analysis light beam (6) can be oriented on a front side of the glass protecting tube (3) parallel to its longitudinal direction.

9. A device according to claim 8, including means for deflecting the analysis light beam (6) from a front side of the glass protection tube (3) to the opposite new entry offset in location into the same front side of the glass protecting tube (3) or for introducing the analysis light beam (3) into a front side of a further glass protecting tube (3) parallel to is longitudinal direction, wherein the detector (5) is placed on the front side of a glass protecting tube (3) from which the analysis light beam (6) comes out last.

10. A device according to claim 9, characterized in that the means for deflecting the analysis light beam (6) comprise a light guiding fiber, a reflector and/or a prism.

11. A device according to claim 8, characterized in that it has a beam splitter for producing a reference light beam between the light source (4) and the front side of the glass protecting tube (3) into which the analysis light beam (6) first comes in, whereby means are provided to guide the reference light beam to the detector (5).

12. A device according to claim 11, characterized in that the light source (4) is a laser light source.

13. A device according to claim 10, characterized in that it has a beam splitter for producing a reference light beam between the light source (4) and the front side of the glass protecting tube (3) into which the analysis light beam (6) first comes in, whereby means are provided to guide the reference light beam to the detector (5).

14. A device according to claim 13, characterized in that the light source (4) is a laser light source.

* * * * *